United States Patent
Lane

(10) Patent No.: US 7,572,462 B2
(45) Date of Patent: *Aug. 11, 2009

(54) PERI-OPERATIVE AND PERI-PROCEDURE NUTRITIONAL SUPPLEMENTATION

(75) Inventor: Edward M. Lane, Weston, CT (US)

(73) Assignee: Judith Lane, Weston, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/723,322

(22) Filed: Mar. 19, 2007

(65) Prior Publication Data

US 2007/0160591 A1    Jul. 12, 2007

Related U.S. Application Data

(63) Continuation of application No. 11/241,939, filed on Oct. 4, 2005, now Pat. No. 7,205,007.

(51) Int. Cl.
    *A61K 36/00* (2006.01)
(52) U.S. Cl. .............. 424/425; 424/602; 424/614; 424/702; 514/167; 514/251; 514/276; 514/458; 514/52; 514/725; 562/562; 562/563
(58) Field of Classification Search .......... None
    See application file for complete search history.

(56) References Cited

U.S. PATENT DOCUMENTS

| | | | |
|---|---|---|---|
| 4,619,829 A | 10/1986 | Motschan | |
| 4,629,625 A | 12/1986 | Gaull | |
| 4,871,550 A | 10/1989 | Millman | |
| 5,215,750 A * | 6/1993 | Keane, II | 424/440 |
| 5,223,285 A | 6/1993 | DeMichele et al. | |
| 5,326,569 A | 7/1994 | Acosta et al. | |
| 5,358,720 A | 10/1994 | Koppel et al. | |
| 5,478,579 A | 12/1995 | Sawruk | |
| 5,494,678 A | 2/1996 | Paradissis et al. | |
| 5,686,429 A | 11/1997 | Lin et al. | |
| 5,821,217 A | 10/1998 | Forse et al. | |
| 5,869,084 A | 2/1999 | Paradissis et al. | |
| 5,948,443 A | 9/1999 | Riley et al. | |
| 5,968,896 A | 10/1999 | Bell et al. | |
| 5,977,073 A * | 11/1999 | Khaled | 514/19 |
| 6,039,978 A | 3/2000 | Bangs et al. | |
| 6,048,846 A | 4/2000 | Cochran | |
| 6,352,713 B1 | 3/2002 | Kirschner et al. | |
| 6,440,450 B1 | 8/2002 | Han et al. | |
| 6,569,857 B1 | 5/2003 | Hermelin et al. | |
| 6,576,666 B2 | 6/2003 | Hermelin et al. | |
| 6,632,459 B2 * | 10/2003 | Graus et al. | 424/728 |
| 7,205,007 B2 * | 4/2007 | Lane | 424/725 |

FOREIGN PATENT DOCUMENTS

WO      WO 98/00858       * 2/1989

OTHER PUBLICATIONS

Translation of WO 89/00858, 1989.*
Grieve, M., "Botanical.com, A Modern Herbal", http://www.botanical.com/botanical/mgmh/a/arnic058.html, 3 pgs, Mar. 4, 2004.
Oberbaum et al., "Homeopathic Treatment in Emergency Medicine: A Case Series," Homeopathy, 92:44-47, 2003.
Seeley et al., "Effect of Homeopathic *Arnica montana* or Bruising in Face-Lifts," Arch. Facial Plast. Surg., 8:54-59, 2006.
"SinEcch", Alpine Pharmaceuticals, http://www.alpinepharm.com, 2 pgs, Mar. 9, 2004.
Snyderman et al., "Reduced Postoperative Infections With An Immune-Enhancing Nutritional Supplement," Laryngoscope, 109:915-921, 1999.
Tveiten et al., "Effect of Arnica D30 in Marathon Runners. Pooled Results From Two Double-Blind Placebo Controlled Studies," Homeopathy, 92:187-189, 2003.
Tveiten et al., "Effect of Arnica D30 on Hard Physical Exercise," Tidsskr. Nor. Laegeforen, 111:3630-3631, 1991.
Wolf et al., "Efficacy of Arnica in Varicose Vein Surgery: Results of a Randomized, Double-blind, Placebo-controlled Pilot Trial", Forsch. Komplementarmed Klass Naturheilkd., 10:242-247, 2003.
"Two New Research Studies Prove That SinEcch Reduces Bruising and Swelling After Liposuction and Facelift Surgery!", Alpine Pharmaceuticals, http://www.alpinepharm.com, 3 pgs, 2002.
"Arnica Montana," Drugs.com, http://www.drugs.com, 2 pgs, Jul. 29, 2006.
"Arnica Montana", Enhancement Media, http://www.yestheyrefake.net/arnica_montana.htm, 5 pgs., Aug. 23, 2003, Mar. 9, 2004.

* cited by examiner

*Primary Examiner*—Susan C Hoffman
(74) *Attorney, Agent, or Firm*—Rothwell, Figg, Ernst & Manbeck, P.C.

(57) ABSTRACT

The invention provides a nutritional supplement system and program for patients undergoing or who have undergone a surgical or other invasive or stressful procedure, or who have suffered an injury. This nutritional supplement for the peri-operative period is designed to prevent deficiencies of nutrients needed for optimal health and healing during this period or for general application and to enable the person receiving the nutritional supplementation to achieve maximum healing and rapid recovery from a procedure or injury.

16 Claims, No Drawings

PERI-OPERATIVE AND PERI-PROCEDURE NUTRITIONAL SUPPLEMENTATION

CROSS REFERENCE TO RELATED APPLICATION

This application is a continuation of U.S. patent application Ser. No. 11/241,939, filed Oct. 4, 2005, now U.S. Pat. No. 7,205,007 which claims priority from PCT/US2004/007136, filed Mar. 10, 2004, U.S. Provisional Application No. 60/461,008, filed Apr. 8, 2003, and U.S. Provisional Application No. 60/492,748, filed Aug. 6, 2003. The disclosures of all of the above parent applications are hereby incorporated by reference in their entirety.

BACKGROUND OF THE INVENTION

1. Technical Field

This invention relates to the field of nutritional supplementation. Specifically, this application describes and claims a nutritional supplement which is specifically tailored to provide nutritional support to an individual during the pre- and post-operative or pre- and post-procedure period (the peri-operative period). The supplements described here may be administered to any person in need of nutritional supplementation, however persons undergoing surgical operations or other types of procedures which cause a stress on the body or persons who have suffered an injury can particularly benefit from the inventive compositions, which promote healing in such persons.

2. Description of the Background Art

The nutritional status of patients affects the outcome of their surgical or interventional procedures, or their response to trauma. One large study documented that at least one complication occurs in 17 percent of surgical patients. The overall risk for surgical complications depends on many individual factors and the type of surgical procedure, however malnourishment or sub-optimal nourishment is an important factor in the incidence of complications. Malnourished patients experience increased morbidity and mortality when faced with the stresses of surgery, interventional procedures, or trauma.

Although the pre-operative or pre-procedure history and physical examination should include an assessment of risk factors for malnutrition, especially in the elderly, nutritional status and the need for nutritional supplementation is hardly ever addressed. While laboratory tests, such as serum albumin and total lymphocyte count, may aid in the diagnosis of malnutrition, other factors should be considered. Social isolation, limited financial resources, poor dentition, weight loss and chronic disorders such as pulmonary disease, congestive heart failure, depression, cognitive disorders, diarrhea, and constipation are commonly associated with malnutrition. In addition, patients often do not and/or cannot eat well for varying periods before and after surgery due to the condition requiring intervention, further compromising nutritional status. Finally, patients are faced with bewildering and often conflicting sources of information concerning nutrition and other factors that would facilitate their speedy and uneventful recovery.

Steps can be taken using natural approaches to strengthen the body before and/or after surgery, interventional procedures, and after injury to enhance defenses, prevent complications, and speed recovery. The wrong choice(s) of nutritional supplementation, however, may have a negative impact on peri-operative or peri-procedure patient care or on general nutrition. For example, Echinacea, ephedra, garlic, gingko, ginseng, kava, St. John's wort, and valerian root are commonly used herbal supplements that may be a reason for concern during the peri-operative and peri-procedure period.

Complications can arise from these herbs' direct and/or pharmacodynamic or pharmacokinetic effects. Direct effects include bleeding from garlic, gingko, and ginseng, cardiovascular instability from ephedra, and hypoglycemia from ginseng, both of which can be dangerous in any individual who may suffer trauma such as that which occurs in injury, surgery or other invasive procedures. Pharmcodynamic herb-drug interactions include potentiation of the sedative effect of anesthetics by kava and valerian root. Pharmacokinetic herb-drug interaction also may induce increased metabolism of many drugs used in the peri-operative or peri-procedure period, for example with St. John's wort.

Micronutrients are elements or compounds which are present in foods in small or trace amounts and include vitamins, minerals or other elements. These micronutrients include compounds such as pantothenic acid, biotin and choline that are found in foods but for which a Recommended Dietary Allowance (RDA) has not yet been determined. Some elements such as Calcium, Sodium, Potassium, Chloride and Phosphorus are consumed in relatively large amounts, while many such as Iron, Iodine, and Zinc are consumed in small amounts (milligrams). Vitamins such as Vitamin B12, and folic acid and the minerals Copper, Selenium and Chromium are consumed in very small, or trace amounts (micrograms). Because the human body does not synthesize many of these micronutrients, they must be obtained from exogenous sources. Micronutrients are an important component of nutrition and are often present in sub-optimal or borderline amounts in the diet of any individual, at least occasionally. During periods of stress to the body, such as illness, injury or stressful surgical or other procedures, levels of these micronutrients may fall below the level necessary for optimal healing.

The primary source of all nutrients is food. Ample evidence documents that a large number of persons of different ages, genders and socioeconomic status cannot or do not obtain the Recommended Dietary Allowance of one or more essential micronutrients from their diet. Furthermore, substantial segments of the population do not demonstrate desirable eating patterns, that is, an adequate intake of the quantity or variety of food to fulfill the Recommended Dietary Allowances. In particular, large groups do not consume the recommended number of dietary servings of fruits and vegetables each day. Other factors such as smoking, physical inactivity, exposure to toxic environmental compounds, the avoidance of certain foods and illness or injury can also contribute to low or deficient intake or absorption of nutrients.

In general, many women do not meet the RDAs for 6 out of 15 micronutrients (B6, vitamin E, Calcium, iron, magnesium and Zinc). Men often fail to meet the RDAs for 4 of 15 micronutrients (B6, vitamin E, magnesium and Zinc). There also is a significant prevalence and incidence in various population subgroups of deficiencies in specific vitamins and minerals, some of which are related to micronutrient deficiency diseases such as scurvy (vitamin C deficiency), pellagra (niacin deficiency), beri-beri (vitamin B1 deficiency), iron deficiency anemia and other vitamin and mineral deficiency states. Thus, vitamin and mineral supplementation has become a recognized method of meeting accepted medical and public health nutrition standards for the general population and/or specific populations. Marginal vitamin and mineral deficiency states, in which the blood or tissue levels are in the low range, may occur without the presence of overt physical signs of deficiency disease, but can result in slow healing or increased incidence of complications from surgery or other procedures.

The nutritional status of a person affects the ability to heal. Yet injury and many medical and dental procedures cause serious stress to the body, often leaving the body in a state of nutritional insufficiency. The body's immune system is weakened and gastrointestinal function is often changed, leaving the body vulnerable to infection and in a state of nutritional insufficiency, thus compromising wound healing and delaying the rate of recovery. Harmful nutritional deficiency is even more likely when the person already is in a state of marginal or sub-optimal nutrition prior to the injury or procedure and when the person is unable to eat normally due to the procedure, for example after oral or gastrointestinal surgery.

It is essential for patients to have proper nutritional supplementation in the peri-operative, peri-procedure, and post-trauma period (and generally) to facilitate wound healing and to expedite recovery while at the same time avoiding those supplements with detrimental or deleterious effects. Therefore, it would be of substantial benefit to provide a nutritional supplement formulation and system which overcomes these deficiencies and is able to provide correct nutritional support for men and women of all ages to promote general health and to maximize the ability to heal and withstand trauma, injury or invasive procedures.

SUMMARY OF THE INVENTION

Accordingly, one embodiment of this invention provides a daily nutritional supplement for administration during the peri-operative period which comprises about 15-500 mg coenzyme Q10; about 250-5000 mg L-cystine; about 250-5000 mg L-glutamine; about 125-5000 mg L-lysine; about 500-10,000 mg Vitamin C; about 2000-10,000 IU Vitamin A; about 100-2000 IU Vitamin D; about 1-10 mg Vitamin B1; about 1-5 mg Vitamin B2; about 5-25 mg Vitamin B5; about 0.5-10 mg Vitamin B6; about 50-25 µg Vitamin B12; about 200-750 µg folic acid; about 185-3750 mg Calcium; about 25-100 µg Selenium; about 12.5-250 mg Zinc; optionally about 200-2000 IU Vitamin E; optionally about 1000-2000 mg eicosapentaenoic acid; optionally about 200-300 mg docosahexaenoic acid; and optionally about 30× $Arnica\ montana$. The nutritional supplement described above may be provided in a single dosage form or in multiple dosage forms.

In another embodiment, the invention provides a daily nutritional supplement which comprises a dosage form comprising about 15-500 mg coenzyme Q10; two dosage forms each comprising about 125-2500 mg L-cystine; two dosage forms each comprising about 125-2500 mg L-glutamine; a dosage form comprising about 125-2500 mg L-lysine; two dosage forms each comprising about 250-5000 mg Vitamin C; a dosage form comprising about 12.5-250 mg Zinc; a dosage form comprising 185-3750 mg Calcium; a dosage form comprising about 100-2,000 IU Vitamin D; two dosage forms each comprising about 2000-10,000 IU Vitamin A, about 1-10 mg Vitamin B1, about 1-5 mg Vitamin B2, about 5-25 mg Vitamin B5, about 0.5-10 mg Vitamin B6, about 50-250 µg Vitamin B12, about 200-750 µg folic acid, and 25-100 µg Selenium; optionally a dosage form comprising 200-2000 IU Vitamin E; optionally a dosage form comprising about 1000-2000 mg eicosapentaenoic acid and about 200-300 mg docosahexaenoic acid; and optionally a dosage form comprising 30× $Arnica\ montana$.

In another embodiment, the invention provides a daily nutritional supplement which comprises about 60 mg coenzyme Q10; about 1000 mg L-cystine; about 1000 mg L-glutamine; about 500 mg L-lysine; about 2000 mg Vitamin C; about 5000 IU Vitamin A; about 400 IU Vitamin D; about 3 mg Vitamin B1; about 1.7 mg Vitamin B2; about 10 mg Vitamin B5; about 2 mg Vitamin B6; about 100 µg Vitamin B12; about 400 µg folic acid; about 750 mg Calcium; about 50 µg Selenium; about 50 mg Zinc; optionally about 600 IU Vitamin E; optionally about 1250 mg eicosapentaenoic acid; optionally about 220 mg docosahexaenoic acid; and optionally about 30× $Arnica\ montana$.

In yet a further embodiment, the invention provides a method of nutritional supplementation of a patient in need thereof which comprises administering to said patient daily, in the peri-operative period, a daily nutritional supplement as described above. Preferably, the peri-operative period is from about two weeks prior to a scheduled surgical operation or procedure to about two weeks subsequent to said surgical operation or procedure or the peri-operative period begins after a physical trauma and continues until substantial healing is completed.

DETAILED DESCRIPTION OF THE PREFERRED EMBODIMENTS

For supplementation to be effective, the supplements provided to the patient should contain suitable amounts of the various micronutrients required by the patient. Suitable amounts can be determined by the skilled physician and depend on the age, gender and general health of the patient., as well as the surgical, dental or other procedure planned for the patient or the degree and type of trauma the patient has suffered. Previous nutritional status also is a factor in determining a suitable amount of nutritional supplementation. In addition, patient compliance is a very important factor, since nutritional supplementation is not effective if the patient does not receive the supplements and is much less effective if the patient does not receive the proper dose on a consistent basis.

Nutritional supplementation preferably is provided in easy-to-use and clearly labeled packs to increase patient compliance. The supplements may be provided for different population groups: men under age fifty, women under age fifty, men over age fifty, and women over age fifty. In addition to these nutritional supplement packs, the treating physician may add other disease-specific supplements as the patient's condition warrants. In addition to the pre-packaged nutritional supplements, the dispensing physician may add other specific supplements if needed.

Nutritional supplements which benefit persons who need to maximize the ability to heal or to withstand trauma or stress to the body preferably should include one or more of the following nutrients: coenzyme Q10, L-cystine, L-glutamine, L-lysine, vitamin C, vitamin A, vitamin D, vitamin E, thiamin, riboflavin, pyridoxine, cyanobalamin, folate, pantothenic acid, Calcium, Selenium and Zinc, and also may include essential fatty acids such as eicosapentaenoic acid (EPA) docosahexaenoic acid (DHA) and the herbal and homeopathic remedy $Arnica\ montana$ in some supplements. See Tables I and II, below.

TABLE I

Preferred Formulations for Identified Patient Groups.

| | Pre-operative | Post-operative |
|---|---|---|
| Men under fifty | Formula A | Formula B |
| over fifty | Formula A | Formula B |
| Women under fifty | Formula A | Formula B |
| over fifty | Formula A | Formula B |

TABLE IIA

Nutritional Supplement Formulation.

| Formula A | Preferred Daily Dosage | Daily Dosage Range | Exemplary Daily Dosages |
|---|---|---|---|
| Coenzyme Q10 | 60 mg | 15-500 mg | 25 mg, 100 mg, 300 mg |
| L-cystine | 1000 mg | 250-5000 mg | 400 mg, 750 mg, 3000 mg |
| L-glutamine | 1000 mg | 250-5000 mg | 500 mg, 1250 mg, 4000 mg |
| L-lysine | 500 mg | 125-2500 mg | 500 mg, 1250 mg, 4000 mg |
| Vitamin C | 2000 mg | 500-10,000 mg | 750 mg, 3000 mg, 7500 mg |
| Vitamin A | 5000 IU | 2000-10,000 IU | 2000 IU, 6000 IU, 8000 IU |
| Vitamin D | 400 IU | 100-2000 IU | 200 IU, 500 IU, 1000 IU |
| Vitamin B1 | 3 mg | 1-10 mg | 2 mg, 4 mg, 7.5 mg |
| Vitamin B2 | 1.7 mg | 1-5 mg | 1.25 mg, 1.5 mg, 2.5 mg |
| Vitamin B5 | 10 mg | 5-25 mg | 7 mg, 12 mg, 20 mg |
| Vitamin B6 | 2 mg | 0.5-10 mg | 1 mg, 3 mg, 5 mg |
| Vitamin B12 | 100 µg | 50-250 µg | 75 µg, 125 µg, 200 µg |
| Folic Acid | 400 µg | 200-750 µg | 250 µg, 500 µg, 600 µg |
| Calcium | 750 mg | 185-3750 mg | 200 mg, 600 mg, 3000 mg |
| Selenium | 50 µg | 25-100 µg | 40 µg, 75 µg, 90 µg |
| Zinc | 50 mg | 12.5-250 mg | 25 mg, 100 mg, 200 mg |

TABLE IIB

Nutritional Supplement Formulation.

| Formula B | Preferred Daily Dosage | Daily Dosage Range | Exemplary Daily Dosages |
|---|---|---|---|
| Coenzyme Q10 | 60 mg | 15-500 mg | 25 mg, 100 mg, 300 mg |
| L-cystine | 1000 mg | 250-5000 mg | 400 mg, 750 mg, 3000 mg |
| L-glutamine | 1000 mg | 250-5000 mg | 500 mg, 1250 mg, 4000 mg |
| L-lysine | 500 mg | 125-2500 mg | 500 mg, 1250 mg, 4000 mg |
| Vitamin C | 2000 mg | 500-10,000 mg | 750 mg, 3000 mg, 7500 mg |
| Vitamin A | 5000 IU | 2000-10,000 IU | 2000 IU, 6000 IU, 8000 IU |
| Vitamin D | 400 IU | 100-2000 IU | 200 IU, 500 IU, 1000 IU |
| Vitamin B1 | 3 mg | 1-10 mg | 2 mg, 4 mg, 7.5 mg |
| Vitamin B2 | 1.7 mg | 1-5 mg | 1.25 mg, 1.5 mg, 2.5 mg |
| Vitamin B5 | 10 mg | 5-25 mg | 7 mg, 12 mg, 20 mg |
| Vitamin B6 | 2 mg | 0.5-10 mg | 1 mg, 3 mg, 5 mg |
| Vitamin B12 | 100 µg | 50-250 µg | 75 µg, 125 µg, 200 µg |
| Folic Acid | 400 µg | 200-750 µg | 250 µg, 500 µg, 600 µg |
| Calcium | 750 mg | 185-3750 mg | 200 mg, 600 mg, 3000 mg |
| Selenium | 50 µg | 25-100 µg | 40 µg, 75 µg, 90 µg |
| Zinc | 50 mg | 12.5-250 mg | 25 mg, 100 mg, 200 mg |
| Vitamin E | 600 IU | 250-2000 IU | 400 IU, 800 IU, 1000 IU |
| Eicosapentaenoic acid | 1250 mg | 1000-2000 mg | 1400 mg, 1750 mg, 1800 mg |
| Docosahexaenoic acid | 220 mg | 200-300 mg | 225 mg, 250 mg, 275 mg |
| *Arnica montana* | 30× | — | — |

Formula A, which is preferably administered in the pre-operative or pre-procedural period contains supplements sufficient to deliver 60 mg/day coenzyme Q10, 1000 mg/day L-cystine, 1000 mg L-glutamine, 500 mg/day L-lysine, 2000 mg/day Vitamin C, 50 mg/day Zinc, 750 mg/day Calcium, 400 IU/day Vitamin D, 5000 IU/day Vitamin A, 3 mg/day thiamin, 1.7 mg/day riboflavin, 2 mg/day pyridoxine, 100 µg/day cyanobalamin, 400 µg/day folic acid, 10 mg/day pantothenic acid and 50 µg/day Selenium. The supplements may be provided in a once-a-day dose or in divided doses to be administered two, three or more times a day. In general, coenzyme Q10, L-lysine, Zinc, Calcium and Vitamin D are given once daily and the remaining nutritional compounds are given twice daily.

Formula B, which is preferably administered in the post-operative, post-procedure or post-trauma period, contains supplements sufficient to deliver the nutritional compounds of formula A above, with the addition of 600 IU/day Vitamin E, essential fatty acids (1250 mg EPA and 220 mg DHA) and *Arnica montana* (30×).

The dosage amounts in these formulas can be modified depending on the judgement of the treating physician and the requirements of the individual patient. More specifically, the daily dosage amounts of one, some, or all of the nutritional compounds can be decreased by 5%, 10%, 20%, 30%, 40%, 50% or up to about 75% or increased by 20%, 40%, 50%, 75%, 100%, 200%, 300%, 400% or up to about 500% of the stated preferred amounts. The formulations of the invention are suitable for most patients but are aimed towards ensuring the maximum ability to recover from a traumatic event. The supplements supply sufficient amounts of the most important nutrients to increase health and ability to heal from events such as traumatic injury, surgery, invasive procedures, burns and the like.

Coenzyme Q10 (ubiquinone) is a compound naturally made in the body which speeds up certain enzymatic reactions. In addition to its role in the metabolic chemical processes, coenzyme Q10 acts as an antioxidant to neutralize cell-damaging molecules known as free radicals. Recent research confirms its efficacy in improving symptoms of Parkinson's Disease. There is additional evidence to suggest efficacy in improving peak oxygen consumption, exercise duration and ejection fraction, which can benefit any person in achieving maximum healing from an injury or trauma.

L-Cystine, L-Glutamine, L-Lysine and L-arginine are amino acids which facilitate wound healing. Glutamine, a non-essential amino acid, is conditionally essential when the metabolic demand for glutamine exceeds the glutamine in the free glutamine pool. During times of metabolic stress (such as surgery, interventional procedures, or trauma), the demand for plasma glutamine markedly increases. The enhanced transport of glutamine to splanchnic organs and to blood cells such as may occur in physical stress results in an intracellular depletion of glutamine in skeletal muscle. Glutamine deficiency can increase the mortality of animals subjected to stress. In critically injured patients, glutamine supplementation reduces nitrogen loss and reduces the mortality rate; in surgical patients, glutamine supplementation improves several immunologic parameters. Thus, glutamine supplements can aid in healing and reduce the chance of infection.

Cystine is composed of two molecules of cysteine joined together. Cystine aids in the production of collagen and other proteins and promotes the proper elasticity and texture of skin. Cystine helps to detoxify harmful toxins and protects the body from radiation damage. It is one of the best free radical destroyers and works best in conjunction with Selenium and Vitamin E. Cystine supplementation also is useful in the treatment of rheumatoid arthritis, atherosclerosis, and cancer. It promotes healing after surgery and burns, chelates heavy metals, and binds to soluble iron, facilitating iron absorption.

Lysine is an essential amino acid that is a necessary building block of all protein. It helps Calcium absorption and maintains proper nitrogen balance in adults. Lysine aids in the production of proteins such as antibodies, hormones, and enzymes, and helps in collagen formation and tissue repair. Because it helps to build muscle protein, it is helpful for those patients recovering from surgery or trauma. It also helps to lower high serum triglyceride levels.

Vitamin C is an antioxidant that is required in at least 300 metabolic functions in the body, including tissue growth and repair. It also aids in the production of anti-stress hormones. It is needed for the metabolism of folate, tyrosine, and phenylalanine. It protects against the harmful effects of pollution, helps to prevent cancer, and protects against infection and promotes the immune system. Essential in the formation of collagens, vitamin C protects against abnormal blood clotting and bruising and promotes the healing of wounds, fractures, and bruises.

Vitamin A is a family of fat-soluble vitamins which includes retinol, retinal, retinoic acid, and carotenoids (including beta-carotene, alpha-carotene and b-cryptoxanthin). As used herein the term "vitamin A" includes mixed carotenoids such as beta-carotene. This nutrient is beneficial for vision, bone growth, cell division and differentiation and also maintains the integrity of certain mucous membranes and skin, which helps to reduce the likelihood of infections. Deficiency of Vitamin A in children can result in damage to the cornea (xerophthalmia), or in less severe cases, night blindness. Even mild Vitamin A deficiency can cause impairment of the immune system; T helper cells are particularly vulnerable. Preferably, nutritional supplements tailored for use in the peri-operative period to increase healing preferably contain 5000 IU vitamin A in the forms discussed above.

Vitamin D, also known as calciferol, is a fat-soluble vitamin that has properties of both a vitamin and a hormone. It is required for the absorption and utilization of Calcium and Phosphorus and promotes mineralization of bone together with other nutrients. Vitamin D is found in several different forms, each with a different activity, and can be converted to an active form in the body. It is necessary for growth, and is especially important for the growth and healing of bones. Unfortunately, Vitamin D deficiency is prevalent, even in people who have few risks of Vitamin D deficiency. Therefore, Vitamin D preferably is included for nutritional supplementation in the peri-operative period.

Vitamin E is an antioxidant important in the prevention of cancer and cardiovascular disease. Alpha-tocopherol is its most active form. It improves circulation and is necessary for tissue repair. It promotes normal blood clotting and healing, reduces scarring from some wounds, and reduces blood pressure. All of these actions can benefit patients in the peri-operative period.

Water-soluble vitamins such as thiamin (vitamin B1), riboflavin (vitamin B2), pyridoxine (vitamin B6), cyanobalamin (vitamin B12), pantothenic acid (vitamin B5) and folic acid also preferably are included in a nutritional supplement for the peri-operative period. Like all the B vitamins, Vitamin B1 (thiamin) assists in releasing energy from dietary fuel sources such as carbohydrates. Vitamin B1 plays a vital role in normal function of the nervous system and muscle tissue. Loss of appetite and fatigue can result from Vitamin B1 deficiency; severe deficiency can cause impaired mental functioning and confusion. Vitamin B2 (riboflavin) also is key to production of energy from food sources (via electron transport) and helps other B vitamins to function most efficiently. Vitamin B2 also supports the production of glutathione, which is important in scavenging of free radicals.

Vitamin B6 is found in the form of pyridoxine, pyridoxal and pyridoxamine and is necessary for the function of more than 100 enzymes involved in protein metabolism. Vitamin B6 also assists in red blood cell metabolism and the nervous and immune systems. Vitamin B6 deficiency can result in anemia due to insufficient production of hemoglobin. Therefore, avoidance of Vitamin B6 deficiency is essential for optimal healing. Vitamin B12 (cobalamin) is necessary for the body to make DNA and maintains nerve and blood cells. Signs of insufficient Vitamin B12 can include fatigue, weakness, poor balance, poor memory and weight loss. Severe B12 deficiency can cause nerve damage. It is therefore important to maintain adequate levels during times of physical stress or injury. Vitamin B5 (pantothenic acid), like most of the B vitamins, is important for conversion of energy, but also is important for formation of lipoproteins and synthesis of certain hormones, and is a component of coenzyme A.

Folic acid, a B vitamin, is necessary for production and maintenance of new cells, which is very important in healing. Folic acid also is important for synthesis of DNA and RNA and in production of red blood cells. Therefore supplementation with this nutrient is particularly desirable during the peri-operative period.

Minerals also can be essential for optimal healing. The minerals Calcium, Selenium and Zinc preferably are contained in a nutritional supplement for the peri-operative period. Calcium participates in the structuring of DNA and RNA. It is vital for the formation of strong bones and teeth. It is also important for the maintenance of a regular heartbeat, the conduction of nerve impulses and for muscular growth and contraction, and is essential for wound healing and tissue repair after trauma.

Selenium is a part of antioxidant enzymes and contributes to essential functioning of the immune system and thyroid gland. Requirements for Selenium increase during stress to the body and therefore preferably is an important component of a nutritional supplement for the peri-operative period in some embodiments. Selenium deficiency can result in poor heart function and thyroid function.

An essential mineral, Zinc is required for protein synthesis and collagen formation, promotes a healthy immune system and assists in wound healing. It is needed for muscular growth and contraction and protects the liver from chemical damage such as which can occur with anesthetics or other drugs or toxins. Zinc also is vital for bone formation. Zinc deficiency contributes to fatigue, susceptibility to infection, and slow wound healing. Therefore, Zinc supplementation is preferred in the peri-operative period.

The omega 3-fatty acids eicosapentaenoic acid (EPA) and docosahexaenoic acid (DHA) are essential fatty acids in man. Besides their nutritional value, they possess beneficial pharmacological effects on the cardiovascular system and development of brain and retina functions, as well as on inflammatory and autoimmune diseases and can beneficially affect mood. EPA and DHA both are preferably included to promote maximum health and healing. Amounts of these important nutrients preferably correspond to a dietary consumption of 2-3 servings per week of fatty fish or about 1250 mg EPA and 220 mg DHA per day. This corresponds to about 3000-4000 mg standardized fish oils per day. Preferably the supplement contains at least 200 mg DHA per day and more preferably about 220-300 mg per day. EPA preferably is present at amounts of about 1000-2000 mg.

*Arnica montana* is an herbal and homeopathic remedy, which has been shown to reduce post-operative bruising and swelling. This herb also can be beneficial to wounds and sprains, and for physical and emotional shock after injury. It promotes healing of damaged tissues, particularly joints and muscles, and can help to control bleeding. This remedy can decrease healing time by encouraging immune cell function and hastening removal of blood and fluids in swollen or bruised tissue.

The nutritional supplements preferably are formulated in one or more convenient dosage forms. Therefore, the term "nutritional supplement" denotes single or multiple dosage forms comprising the nutrient compounds that make up the supplement. The term "daily nutritional supplement" refers to one or more dosage forms containing sufficient nutritional compounds for one day, whether the supplement is in the form of a single dose (of one or more dosage forms) or divided doses (each comprising one or more dosage forms) for administration in one day. The term "nutritional supplement system" refers to a program for supplementation that comprises the nutritional supplement(s) as defined above. The term "dosage form" encompasses any means effective for the administration of the nutritional supplement. Oral dosage forms are preferred and include, but are not limited to, one or more of the following: tablets, hard capsules, soft capsules, caplets, lozenges, chewable tablets, solutions, suspensions, syrups, tinctures, oils, powders, granules, beads, liposomes and the like. Alternatively, the dosage form or forms may be for other routes of administration such as intravenous, transdermal, transmucosal or any route that is suitable given the patient to be supplemented. Alternative dosage forms therefore may include intravenous solutions, transdermal patches, implants and the like. The dosage forms may contain suitable inert ingredients or excipients such as are known in the pharmaceutical arts. Preferred solid dosage forms are composed of at least one carrier which may advantageously contain one or more substances which act as diluents, flavoring agents, solubilizers, lubricants, suspending agents, binders, disintegrating agents and the like, as is known in the art. The solid carrier material also may includes encapsulating material.

The nutritional supplement may be supplied in a single dosage form or in multiple dosage forms, for example 2-19 separate dosage forms. Any dosage form or group of dosage forms is designed to deliver an effective dose of the nutritional compounds in the supplement. An effective amount varies with the type of patient. Therefore, the nutritional supplements of the invention may be tailored to particular groups or time periods. See Table I. For general use, however the supplement of Formula A is suitable. The supplements may be provided in a once-a-day dose or in divided doses to be administered two, three or more times per day. Formulations designed to provide extended or slow release may be provided for any or all of the components of the nutritional supplement.

In general, for most surgical operations, dental procedures or other stressful procedures, the nutritional supplementation is administered to the patient for one week or more prior to a scheduled operation or procedure, depending on the general health and nutritional status of the patient. For example, supplements may be given for one day, two days, or any number of days from 3 to about 15 or more days prior to a scheduled operation or procedure. Supplementation preferably is continued for at least one week post-operatively, but may be administered for 1 day or longer, for example any number of days from 2-15 days or until the desired healing has taken place. In the case of an unexpected trauma or emergency surgery, nutritional supplementation cannot be planned prior to the incident, however the nutritional supplements of this invention may be administered after trauma or unexpected surgery or unplanned procedure for the same period of time discussed above. Therefore, the terms "pre-operative," "post-operative" and "peri-operative" as used herein refer to the period of time surrounding any surgical operation, invasive procedure or physical trauma.

Exemplary operations and procedures may include, but are not limited to general surgery (i.e. hernia, gall bladder), plastic surgery (i.e. partial or full face lift, liposuction), orthopedic surgery (i.e. joint replacement, tendon repair), urologic surgery (i.e. trans-urethral resection prostate) ophthalmic surgery (i.e. cataracts, laser vision correction), ear, nose and throat surgery (i.e. nasal septum, turbinate reduction), neurosurgery (i.e. craniotomy, procedures on discs or vertebral spaces), cardiovascular procedures (i.e. coronary artery angioplasty) gastrointestinal surgery and procedures (i.e. upper endoscopy, colonoscopy), oral and maxillo-facial surgery and procedures (i.e. dental extractions and restorations, prophylaxis and cleaning, orthodontic, periodontic and endodontic procedures, dental implants, care for carious teeth, gingivitis, and mucosal diseases) and the like. Physical trauma (such as trauma due to car accidents, gunshot wounds, falls, burns and the like) also are included in the term "surgical operation, invasive procedure or traumatic event."

The time period may span 2-4 weeks before to 2-4 weeks after the event or until substantial healing has occurred or may begin shortly after the event and continue 2-4 weeks or until substantial healing has occurred. Substantial healing has occurred when the wound is stable, for example after suture removal, and all swelling, redness, tenderness and pain is gone and the patient is able to resume normal activities. Shorter time periods also are contemplated as described herein, for example, 1 week before to 1 week after, 3 days before to 3 days after, 2 weeks before to 4 weeks after, immediately after to 1 week after, and so on. The peri-operative period generally is a period of time sufficient to obtain optimal nutrition in the fluids and tissues of the body prior to the trauma, when possible, and to obtain or maintain this optimal nutrition for sufficient time to allow healing to occur after the trauma.

The dosage forms of the invention may be packaged for convenience for twice daily or daily dosing or other dosing schedules as determined by the physician taking into consideration factors such as convenience, efficacy, the dosage form and type, and patient compliance. Preferably, the supplements are packaged in groups to be administered at one time for ease of compliance and may be labeled to include the day or time of administration, or both. Packages preferably are easy-to-open and protective against light, air and moisture.

To improve the chances that this supplementation is used correctly and most beneficially, it is preferred also to supply educational support for the supplementation, particularly if the patient is new to supplementation. Educational material may accompany the nutritional supplements and may include a brochure and optionally a CD and/or DVD that provides the patient with more detailed information about the nutritional supplement system and why its use is important to rapid recovery. Generally, the brochure should provide an overview concerning the importance of nutritional supplementation and the rationale for using the specific regimen provided to the patient as well as a clear description of proper use of the supplements. Optionally included in the nutritional supplements or nutritional supplement kits is a CD or DVD which provides to the patient more detailed information about the nutritional supplement system and why the supplement is important to rapid recovery. The educational supports preferably are designed to supplement the teaching offered by the treating physician.

A web site may be provided and referenced in the brochure and/or CD/DVD to reiterate information and include links to informational web sites. These web sites may include reference as to the scientific basis for the supplementation system and answer commonly asked questions concerning disease, surgery, dentistry and dental procedures, interventional procedures, and trauma. Other links can direct patients to expert faculty or a help line who will be able to answer general supplementation and other nutritional questions.

EXAMPLES

Example 1

Nutritional Supplementation for Peri-Operative Patients.

Preferred nutritional supplements for the peri-operative period contain a daily dosage of 15-500 mg Coenzyme Q10, 250-5000 mg L-cystine, 250-5000 mg L-glutamine, 125-2500 mg L-lysine, 500-10,000 mg Vitamin C, 2000-10,000 IU Vitamin A, 100-2000 IU Vitamin D, 1-10 mg Vitamin B1, 1-5 mg Vitamin B2, 5-25 mg Vitamin B5, 0.5-10 mg Vitamin B6, 50-250 µg Vitamin B12, 200-750 µg folic acid, 185-3750 mg Calcium, 25-100 µg Selenium and 12.5-250 mg Zinc. The supplement is provided in multiple oral dosage forms for once daily or twice daily administration.

Example 2

Nutritional Supplementation for Peri-Operative Patients.

Most preferred nutritional supplements for the peri-operative period contain a daily dosage of 60 mg Coenzyme Q10, 1000 mg L-cystine, 1000 mg L-glutamine, 500 mg L-lysine, 2000 mg Vitamin C, 5000 IU Vitamin A, 400 IU Vitamin D, 3 mg Vitamin B1, 1.7 mg Vitamin B2, 10 mg Vitamin B5, 2 mg Vitamin B6, 100 µg Vitamin B12, 400 µg folic acid, 750 mg Calcium, 50 µg Selenium and 50 mg Zinc. The supplement is provided in multiple oral dosage forms for once daily or twice daily administration.

Example 3

Nutritional Supplementation for Peri-Operative Patients.

Preferred nutritional supplements for the peri-operative period contain a daily dosage of 15-500 mg Coenzyme Q10, 250-5000 mg L-cystine, 250-5000 mg L-glutamine, 125-2500 mg L-lysine, 500-10,000 mg Vitamin C, 2000-10,000 IU Vitamin A, 100-2000 IU Vitamin D, 1-10 mg Vitamin B1, 1-5 mg Vitamin B2, 5-25 mg Vitamin B5, 0.5-10 mg Vitamin B6, 50-250 µg Vitamin B12, 200-750 µg folic acid, 185-3750 mg Calcium, 25-100 µg Selenium, 12.5-250 mg Zinc, 250-2000 IU Vitamin E, 1000-2000 mg Eicosapentaenoic acid, 200-300 mg Docosohexaenoic acid and 30× *Arnica montana*. The supplement is provided in multiple oral dosage forms for once daily or twice daily administration.

Example 4

Nutritional Supplementation for Peri-Operative Patients.

Most preferred nutritional supplements for the peri-operative period contain a daily dosage of 60 mg Coenzyme Q10, 1000 mg L-cystine, 1000 mg L-glutamine, 500 mg L-lysine, 2000 mg Vitamin C, 5000 IU Vitamin A, 400 IU Vitamin D, 3 mg Vitamin B1, 1.7 mg Vitamin B2, 10 mg Vitamin B5, 2 mg Vitamin B6, 100 µg Vitamin B12, 400 µg folic acid, 750 mg Calcium, 50 µg Selenium, 50 mg Zinc, 600 IU Vitamin E, 1250 mg Eicosapentaenoic acid, 220 mg Docosohexaenoic acid and 30× *Arnica montana*. The supplement is provided in multiple oral dosage forms for once daily or twice daily administration.

The invention claimed is:

1. A daily nutritional supplement which comprises:
   a) about 2000-10,000 IU Vitamin A;
   b) about 1-10 mg Vitamin B1;
   c) about 0.5-10 mg Vitamin B6;
   d) about 50-250 µg Vitamin B12;
   e) about 500-10,000 mg Vitamin C;
   f) about 250-5000 mg L-glutamine; and
   g) about 30X *Arnica Montana*.

2. The daily nutritional supplement of claim 1 which further comprises a nutrient selected from the group consisting of:
   h) about 1-5 mg Vitamin B2;
   i) about 5-25 mg Vitamin B5;
   j) about 200-750 µg folic acid;
   k) about 100-2000 IU Vitamin D;
   I) about 200-2000 IU Vitamin E;
   m) about 15-500 mg coenzyme Q10;
   n) about 25-100 µg Selenium;
   o) about 12.5-250 mg Zinc;
   p) about 185-3750 mg Calcium;
   q) about 125-5000 mg L-lysine;
   r) about 250-5000 mg L-cystine;
   s) about 1000-2000 mg eicosapentaenoic acid;
   t) about 200-300 mg docosahexaenoic acid; and
   u) any combination thereof.

3. A daily nutritional supplement of claim 1 which comprises:
   a) about 5000 IU Vitamin A;
   b) about 3 mg Vitamin B1;
   c) about 2 mg Vitamin B6;
   d) about 100 µg Vitamin B12;
   e) about 2000 mg Vitamin C;
   f) about 1000 mg L-glutamine; and
   g) about 30X *Arnica montana*.

4. The daily nutritional supplement of claim 3 which further comprises a nutrient selected from the group consisting of:
   h) about 1.7 mg Vitamin B2;
   i) about 10 mg Vitamin B5;
   J) about 400 µg folic acid;
   k) about 400 IU Vitamin D;
   I) about 600 IU Vitamin E;

m) about 60 mg coenzyme Q10;
n) about 50 μg Selenium;
o) about 50 mg Zinc;
p) about 750 mg Calcium;
q) about 500 mg L-lysine;
r) about 1000 mg L-cystine;
s) about 1250 mg eicosapentaenoic acid;
t) about 220 mg docosahexaenoic acid; and
u) any combination thereof.

5. The daily nutritional supplement of claim 1 which is provided in a single dosage form.

6. The daily nutritional supplement of claim 3 which is provided in a single dosage form.

7. The daily nutritional supplement of claim 1 which is provided in multiple dosage forms.

8. The daily nutritional supplement of claim 3 which is provided in multiple dosage forms.

9. The daily nutritional supplement of claim 7 which comprises:
   a) two dosage forms each comprising about 1000-5000 IU Vitamin A, about 0.5-5 mg Vitamin B1, about 0.25-5 mg Vitamin B6, about 25-125 μg Vitamin B12;
   b) two dosage forms each comprising about 250-5000 mg Vitamin C; and
   c) two dosage forms each comprising about 125-2500 mg L-glutamine.

10. The daily nutritional supplement of claim 9 which comprises:
    a) two dosage forms each comprising about 1000-5000 IU Vitamin A, about 0.5-5mg Vitamin B1, about 0.25-5 mg Vitamin B6, about 25-125 μg Vitamin B12 and each further comprising about 0.5-2.5 mg Vitamin B2, about 2.5-12.5 mg Vitamin B5 and about 100-375 μg folic acid;
    b) two dosage forms each comprising about 250-5000 mg Vitamin C;
    c) two dosage forms each comprising about 125-2500 mg L-glutamine; and which further comprises:
    d) a dosage form comprising about 100-2,000 IU Vitamin D;
    e) a dosage form comprising about 200-2,000 IU Vitamin E;
    f) a dosage form comprising about 15-500 mg coenzyme Q10;
    g) a dosage form comprising about 25-100 μg Selenium and about 12.5-250 mg Zinc;
    h) a dosage form comprising about 185-3750 mg Calcium;
    i) a dosage form comprising about 125-2500 mg L-lysine;
    j) two dosage forms each comprising about 125-2500 mg L-cystine;
    k) a dosage form comprising about 1000-2000 mg eicosapentaenoic acid and about 200-300 mg docosahexaenoic acid; and
    l) a dosage form comprising about 30X *Arnica montana*.

11. The daily nutritional supplement of claim 8 which comprises:
    a) two dosage forms each comprising about 2500 IU Vitamin A, about 1.5 mg Vitamin B1, about 1 mg Vitamin B6, and about 50 μg Vitamin B12;
    b) two dosage forms each comprising about 1000 mg Vitamin C; and
    c) two dosage forms each comprising about 500 mg L-glutamine.

12. The daily nutritional supplement of claim 11 which comprises:
    a) two dosage forms each comprising about 2500 IU Vitamin A, about 1.5 mg Vitamin B1, about 1 mg Vitamin B6, about 50 μg Vitamin B12 and each further comprising about 0.85 mg Vitamin B2, about 5 mg Vitamin B5 and about 200 μg folic acid;
    b) two dosage forms each comprising about 1000 mg Vitamin C;
    c) two dosage forms each comprising about 500 mg L-glutamine and which further comprises;
    d) a dosage form comprising about 400 IU Vitamin D;
    e) a dosage form comprising about 600 IU Vitamin E;
    f) a dosage form comprising about 60 mg coenzyme Q10;
    g) a dosage form comprising about 50 μg Selenium and about 50 mg Zinc;
    h) a dosage form comprising about 750 mg Calcium;
    i) a dosage form comprising about 500 mg L-lysine;
    j) two dosage forms each comprising about 500 mg L-cystine;
    k) a dosage form comprising about 1250 mg eicosapentaenoic acid and about 220 mg docosahexaenoic acid; and
    l) a dosage form comprising about 30X *Arnica montana*.

13. A method of nutritional supplementation of an individual in need thereof, which comprises administering a daily nutritional supplement of claim 1.

14. A method of nutritional supplementation of an individual in need thereof, which comprises administering a daily nutritional supplement of claim 3.

15. A method of nutritional supplementation of an individual in need thereof, which comprises administering a daily nutritional supplement of claim 9.

16. A method of nutritional supplementation of an individual in need thereof, which comprises administering a daily nutritional supplement of claim 11.

* * * * *